US010775394B2

(12) United States Patent
Benchikh et al.

(10) Patent No.: US 10,775,394 B2
(45) Date of Patent: Sep. 15, 2020

(54) IMMUNOASSAY FOR PHENETHYLAMINES OF THE 2C AND DO SUB-FAMILIES

(71) Applicant: Randox Laboratories Limited, Crumlin (GB)

(72) Inventors: Elouard Benchikh, Crumlin (GB); Peter Fitzgerald, Crumlin (GB); Ivan McConnell, Crumlin (GB); Philip Lowry, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 251 days.

(21) Appl. No.: 15/928,595

(22) Filed: Mar. 22, 2018

(65) Prior Publication Data

US 2018/0209998 A1 Jul. 26, 2018

Related U.S. Application Data

(62) Division of application No. 14/451,964, filed on Aug. 5, 2014, now Pat. No. 9,945,877.

(30) Foreign Application Priority Data

Aug. 5, 2013 (GB) .................................. 1313938.1

(51) Int. Cl.
*G01N 33/94* (2006.01)
*C07K 16/44* (2006.01)

(52) U.S. Cl.
CPC ............. *G01N 33/94* (2013.01); *C07K 16/44* (2013.01); *G01N 33/946* (2013.01); *C07K 2317/33* (2013.01); *G01N 2430/00* (2013.01)

(58) Field of Classification Search
CPC ................. C07K 16/44; C07K 2317/33; G01N 2430/00; G01N 33/94; G01N 33/946
See application file for complete search history.

(56) References Cited

U.S. PATENT DOCUMENTS

| 3,996,344 | A | 12/1976 | Gross |
| 4,016,146 | A | 4/1977 | Soares |
| 4,041,076 | A | 8/1977 | Avenia et al. |
| 2003/0170728 | A1 | 9/2003 | McConnell et al. |
| 2004/0077021 | A1 | 4/2004 | Hui et al. |
| 2004/0121400 | A1 | 6/2004 | McConnell et al. |
| 2015/0346226 | A1 | 12/2015 | McConnell et al. |

FOREIGN PATENT DOCUMENTS

EP 0399184 9/1995

OTHER PUBLICATIONS

Blaazer, et al., Structure-Activity Relationships of Phenylalkylamines as Agonist Ligands for 5-HT2A Receptors, ChemMedChem, vol. 3, No. 9, pp. 1299-1309 Sep. 1, 2008.
Fitzgerald, et al., Development of a High-Throughput Automated Analyzer Using Biochip Array Technology, Clinical Chemistry, vol. 51, No. 1, pp. 1165-1176 Jul. 1, 2005.
Fujiwara, et al., Enzyme immunoassay for the quantification of mitomycin C using beta-galactosidase as a label, Cancer Research, vol. 42, No. 4, pp. 1487-1491 Apr. 1, 1982.
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.
Hill, et al., Severe clinical toxicity associated with analytically confirmed recreational use of 25I-NBOMe: case series, Cinical toxicology, vol. 51, No. 6, pp. 487-492 Jul. 1, 2013.
Kim, et al., Synthesis of haptens for immunoassay of organophosphorus pesticides and effect of heterology in hapten spacer arm length on immunoassay sensitivity, Analytica chimica ACTA, vol. 475, No. 1, pp. 85-96 Jan. 1, 2003.
Nolli, et al., Antibodies against the antibiotics: an overview, Annali Dell'Istituto Superiore di Sanita, vol. 27, No. 1, pp. 149-154 Jan. 1, 1991.
Peterson et al., "Using Hapten Design to Discover Therapeutic Monoclonal Antibodies for Treating Methamphetamine Abuse," J. Pharmacology and Exp. Therap., 322:30-39 (2007).
Petrie et al., Cross-reactivity studies and predictive modeling of "Bath Salts" and other amphetamine-type stimulants with amphetamine screening immunoassays, 2013, 83-91, Clinical Toxicology, vol. 51, Informa Healthcare USA, Inc.
Poklis, et al., High-Performance Liquid Chromatography with Tandem Mass Spectrometry for the Determination of Nine Hallucinogenic 25-NBOMe Designer Drugs in Urine Specimens, Journal of Analytical Toxicology, vol. 38, No. 3, pp. 113-121 Apr. 1, 2014.
Randox Toxicology, DOx Series ELISA Kit, Feb. 16, 2014, 1-2, Randox Toxicology Ltd., Crumlin, United Kingdom.
Rao, "Immunology," 2005, p. 69.
Riceberg et al., "Radioimmunoassays of 3,4,5-Trimethoxyphenethylamine (Mescaline) and 2,5-Dimethoxy-4-Methylphenyl-isopropylamine (DOM)," Analytical Biochemistry, 60:551-559, Mar. 6, 1974.
Swortwood, Hearn & DeCaprio, Cross-reactivity of designer drugs, including cathinone derivatives, in commercial enzyme-linked immunosorbent assays, 2013, Drug Testing and Analysis, John Wiley & Sons, Ltd.
Vorce et al., Dimethylamylamine: A Drug Causing Positive Immunoassay Results for Amphetamines, Apr. 2011, 183-187, J. of Analytical Toxicology, vol. 35.

*Primary Examiner* — Galina M. Yakovleva
(74) *Attorney, Agent, or Firm* — Gavrilovich, Dodd & Lindsey LLP

(57) ABSTRACT

Immunoassay methods and their requisite components for the detection and determination of phenethylamines of the 2C and DO sub-families are described.

13 Claims, 7 Drawing Sheets

MDMA　　　　　　　　　Cathinone　　　　　　　　Methcathinone

2C-I　　　　　　　　　　　DOB

Phenethylamine sub-structure　　　Amphetamine　　　　　　Methamphetamine

Mephedrone　　　　　　　　　　　　MDPV

TMA　　　　　　　　Trimethoxyphenethylamine (mescaline)

| R= Nitro | 2C-N | R'= Me | DOM |
| R= F | 2C-F | R'= Br | DOB |
| R= H | 2C-H | R'= I | DOI |
| R= Me | 2C-D | R'= Bu | DOBu |
| R= Br | 2C-B | R'= Et | DOEt |
| R= I | 2C-I | R'= Cl | DOC |
| R= S-Me | 2C-T | R'= CN | DOCN |
| R= Et | 2C-E | R'= propyl | DOPr |
| R= Cl | 2C-C | R'= NO2 | DON |
| R= CN | 2C-CN | R'= isopropyl | DOIp |
| R= propyl | 2C-P | R'= CF3 | DOTFM |
| R= S-Et | 2C-T-2 | R'= CH2CH2F | DOEf |
| R= S-propyl | 2C-T-7 | R'= O-Me | |
| R= CF3 | 2C-TMF | | |
| R= CH2CH2F | 2C-T-21 | | |
| R= S-isopropyl | 2C-T4 | | |
| R= isopropyl | 2C-O4 | | |

2C sub-family          DO sub-family

Hapten-1          Hapten-2

Hapten-3          Hapten-4

Immunogen of Example 10

Immunogen of Example 21

IMMUNOASSAY FOR PHENETHYLAMINES OF THE 2C AND DO SUB-FAMILIES

CROSS REFERENCE TO RELATED APPLICATIONS

This application is a divisional of U.S. patent application Ser. No. 14/451,964, filed Aug. 5, 2014, which claims priority under 35 U.S.C. § 119 to United Kingdom Application No. GB1313938.1 filed Aug. 5, 2013, the disclosures of which are incorporated herein by reference.

BACKGROUND TO THE INVENTION

Figure 1:
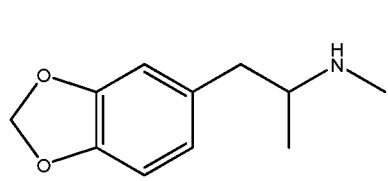
Figure 1:
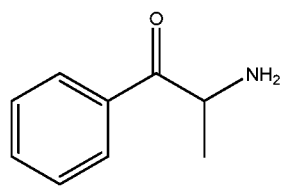
Figure 1:
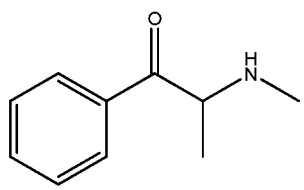
Figure 1:
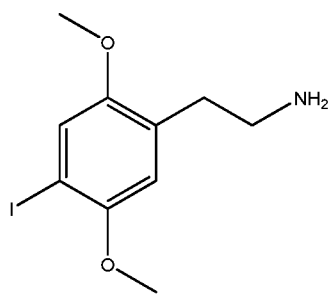
Figure 1:
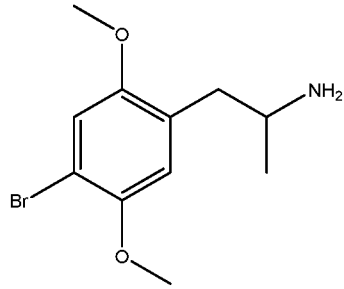
Figure 1:
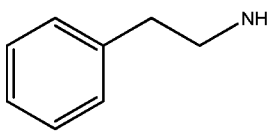
Figure 1:
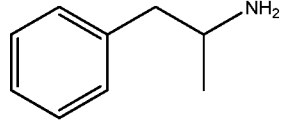
Figure 1:
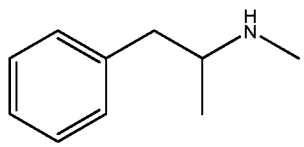
Figure 1:
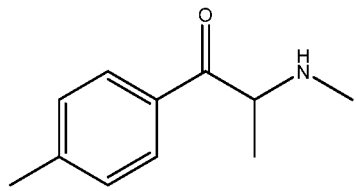
Figure 1:
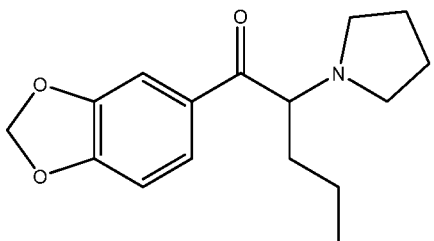
Figure 1:
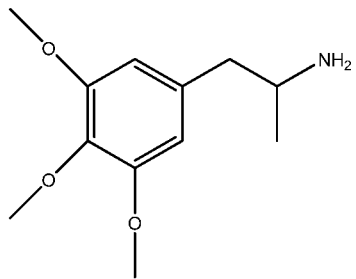
Figure 1:
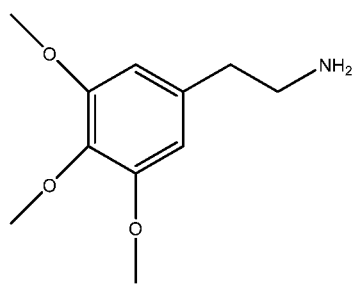

The invention relates to the field of analytical detection of psychoactive drugs of the phenethylamine family. Specifically, immunodetection of 2C and DO phenethylamines, sub-families of the phenethylamines, is described. The psychoactive phenethylamines represent a large family of drugs, each member incorporating the phenethylamine sub-structure (FIG. 1) and are exemplified by the legal, but abused, therapeutic drugs amphetamine and methamphetamine, the plant-derived compounds cathinone and mescaline (3,4,5-trimethoxyphenethylmine) and the designer drugs MDMA and mephedrone. The large number of phenethylamines can be approximately classified to sub-families according to the nature of the chemical substituents on the basic phenethylamine sub-structure;—
- the methylenedioxy-phenethylamines represented by MDMA,
- the β-keto-phenethylamines represented by cathinone/mephedrone/methcathinone, including pyrrolidinophenones, typically classified as a sub-set of the synthetic cathinones, such as RS)-1-(benzo[d][1,3]dioxol-5-yl)-2-(pyrrolidin-1-yl)pentan-1-one (commonly referred to as 3,4-methylenedioxypyrovalerone or MDPV (see EP Patent publication 2626358) and
- the 2,5-dimethoxy-phenethylamines represented by, for example, 1-(2,5-dimethoxy-4-iodophenyl)ethan-2-amine (2C-I) and 1-(4-bromo-2,5-dimethoxyphenyl)propan-2-amine (DOB) (FIG. 1).

Detection of the psychoactive phenethylamines is a necessary component in the clinical and forensic toxicological fields and is finding increasing use in work-place testing to support health and safety. The main analytical technique used for identifying individual psychoactive phenethylamines is mass spectrometry (MS). This expensive and specialised confirmatory technique is generally preceded by the immunoassay, a cheaper and simpler technique using antibodies with both generic and molecule-specific detection capabilities.

There are currently immunoassay based methods for several sub-families of the phenethylamine class of psychoactive drugs, including mephedrone/cathinone (European Patent No. 2442110), the pyrrolidinophenones, typically classified as a sub-set of the synthetic cathinones (see EP Patent publication 2626358), the amphetamines and MDMA (European Patent No. 1321772). Depending on the application, either generic or molecule-specific antibodies may be desirable. For a comprehensive pre-screen where there are tens of molecules in a family, generic antibodies might be preferred with MS used subsequently to identify an individual molecule. Alternatively, where the requirement might be to identify a sub-family of molecules; an immunoassay specific to the sub-family could preclude, or better support, subsequent analysis by MS.

Swortwood et al 2013, at Table 7, examines the cross-reactivity for a Randox MDPV kit (all tested members of the DO and 2C sub-families show less than 0.1% cross-reactivity. Specifically, of the DO sub-family, each of tested (±)-DOET, (±)-DOM and (±)-DOB show less than 0.1% cross-reactivity when compared to 100% for (±)-MDPV and, of the 2C sub-family, each of tested 2C-E, 2C-B and 2C-T-7 show less than 0.1% cross-reactivity when compared to 100% for (±)-MDPV. Swortwood et al 2013, at Table 7, also examines the cross-reactivity for a Randox mephedrone/methcathinone kit (all tested members of the DO and 2C sub-families show less than 0.0125% cross-reactivity). Specifically, of the DO sub-family, each of tested (±)-DOET, (±)-DOM and (±)-DOB show less than 0.0125% cross-reactivity when compared to 100% for (±)-mephedrone and, of the 2C sub-family, each of tested 2C-E, 2C-B and 2C-T-7 show less than 0.0125% cross-reactivity when compared to 100% for (±)-mephedrone. Swortwood et al 2013 concludes that there are no current phenethylamine immunoassays dedicated to the detection of, separately, members of the 2C and DO sub-families.

Petrie et al 2013, at Table 1, reviews cross-reactivity of "bath salts" using commercially available amphetamine screening immunoassays—AxSYM amphetamine/methamphetamine II assay (Abbott); CEDIA amphetamine/ecstasy immunoassay (Thermo Fisher); and EMIT II Plus amphetamines assay (Siemens). The AxSYM assay does not show cross-reactivity to any tested member of either the DO sub-family (DOB, DOEt and DOM) or the 2C sub-family (2C-I, 2C-B, 2C-T-2, 2C-T-4, 2C-T-7 and 2C-H), even when tested at 5,000 ng/mL. The EMIT and CEDIA amphetamine assays have been shown to weakly bind to both 2C and DO sub-family members when tested at concentrations of 5,000 ng/ml (Petrie et al 2013). The CEDIA assay shows cross-reactivities of none (2C-I), 3.0% (2C-B) 2.2% (2C-T-2), 2.2% (2C-T-4), 2.8% (2C-T-7) and 3.1% (2C-H) for the 2C sub-family and shows very slightly higher cross-reactivities of 8.5% (DOB), 4.8% (DOEt) and 3.9% (DOM) for the DO sub-family. The EMIT assay shows cross-reactivities of 28.6% (2C-I), 36.0% (2C-B), 11.7% (2C-T-2), none (2C-T-4), 18.1 (2C-T-7) and none (2C-H) for the 2C sub-family and shows very slightly higher cross-reactivities of 39.1% (DOB), 18.8% (DOEt) and 23.2% (DOM) for the DO sub-family, albeit at very high and unrealistic concentrations. Each of the AxSYM, CEDIA and EMIT II Plus assays were tested at 5,000, 20,000 and 100,000 ng/mL. Petrie et al 2013 admits a urinary level of 100,000 ng/mL would likely only be encountered in severe overdose cases. None of the AxSYM, CEDIA and EMIT II Plus assays can be used to discriminate between drugs of the DO and 2C sub-families. This lack of sensitivity and specificity to a single sub-family (either 2C or DO) precludes the CEDIA and EMIT assays from being practically applied to detect, and discriminate between 2C and DO drugs. The inability to even bind to tested members of the DO and 2C sub-families precludes the use of AxSYM assay as a screen for members of either the DO and 2C sub-families.

A further problem facing immunodetection of phenethylamines is the potential for antibodies to exhibit unexpected and undesirable cross-reactivity to common nutritional supplements and commonly prescribed medicines giving rise to false positive assay results. For example, the anorectic dimethylamylamine has been shown to cross-react with amphetamine immunoassays (Vorce et al 2011).

Thus, there is a need for the sensitive and selective immunodetection of 2C and DO drugs, while avoiding unwanted cross-reactivity.

REFERENCES

Petrie M, Lynch K L, Ekins S, Chang J S, Goetz R J, WU A H B and Krasowski M D (2013). Clinical Toxicology, 51: 83-91.
Swortwood M J, Hearn W L and DeCaprio A P. (2013). Drug testing and Analysis. May, DOI: 10.1002/dta.1489.
Vorce S P, Holler J M, Cawrse B M and Magluiglio Jr J (2011). Journal of Analytical Toxicology, 35: 183-187.

DRAWINGS

Figure 2:
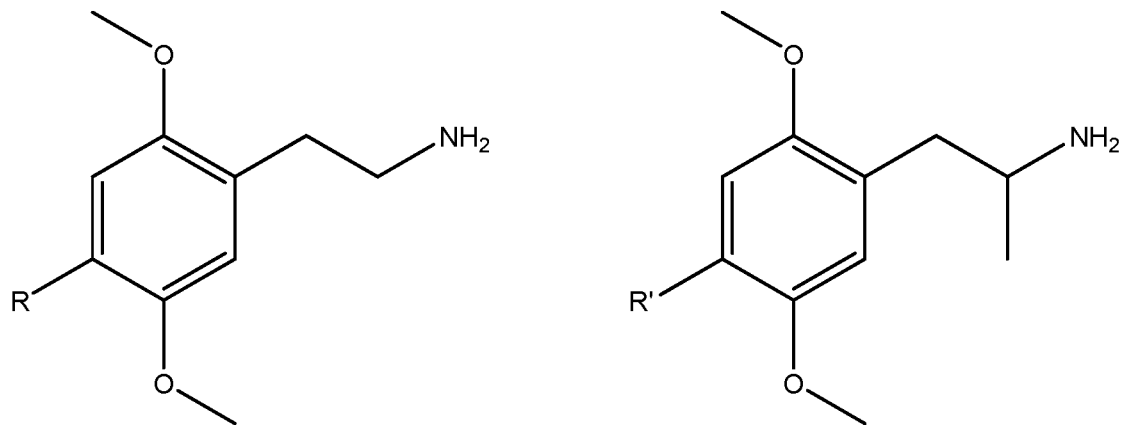
Figure 3:
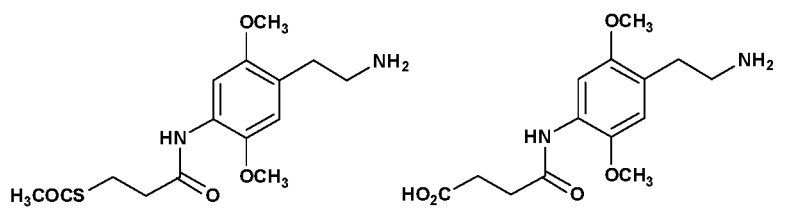
Figure 3:
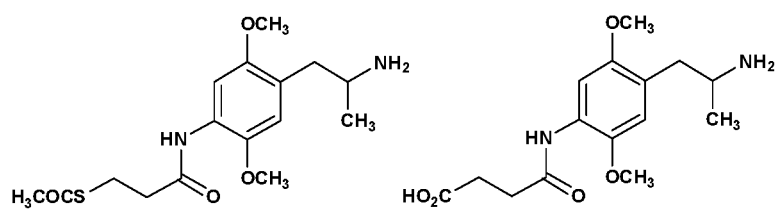
Figure 3:
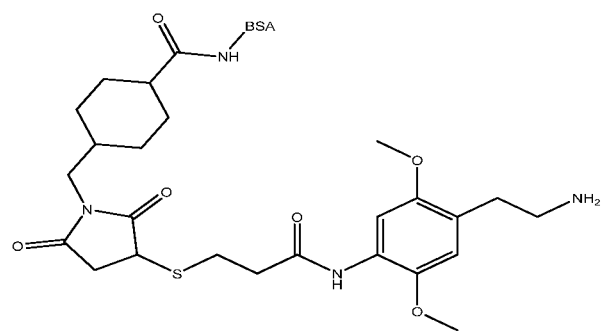
Figure 3:
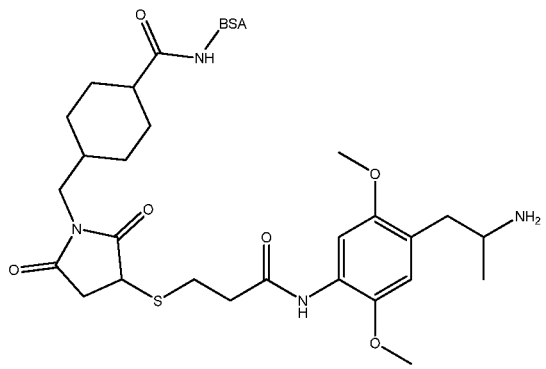
Figure 4:
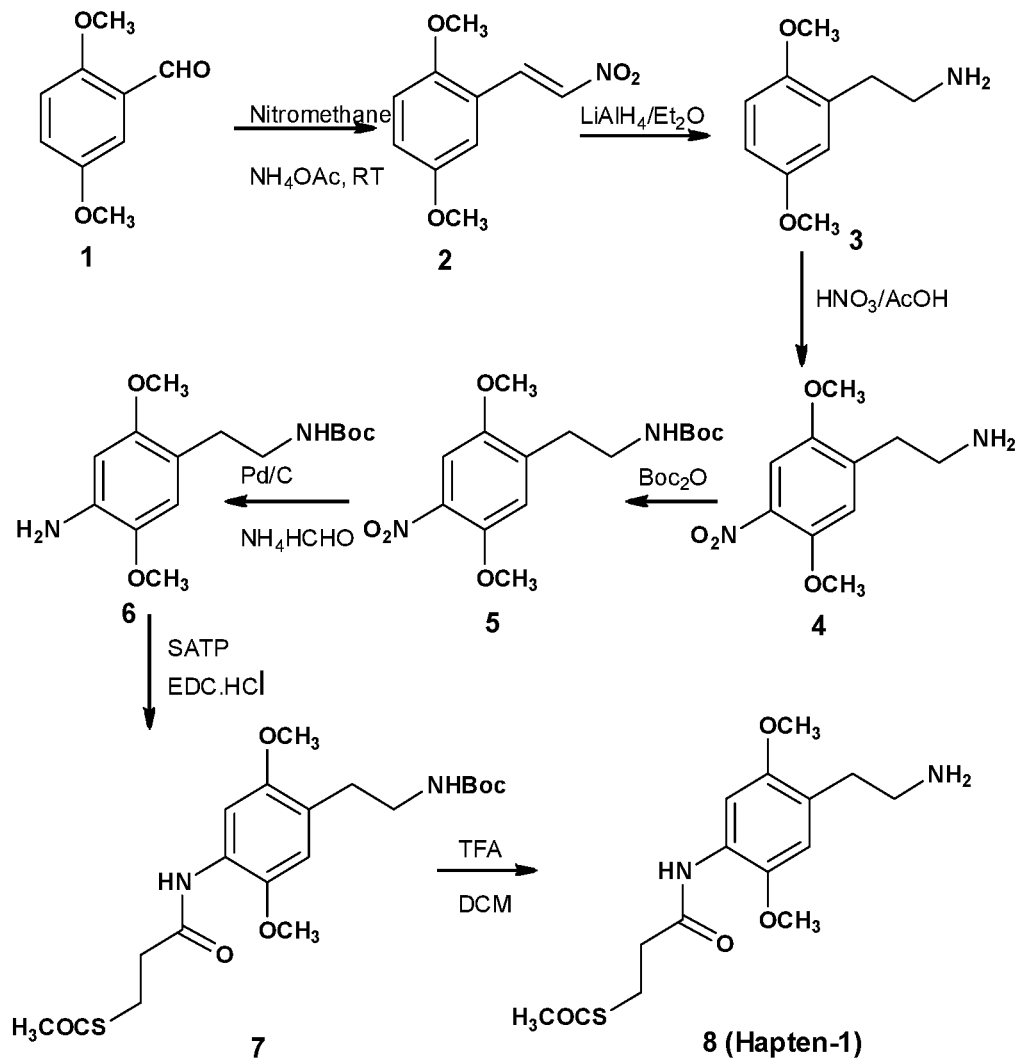
Figure 5:
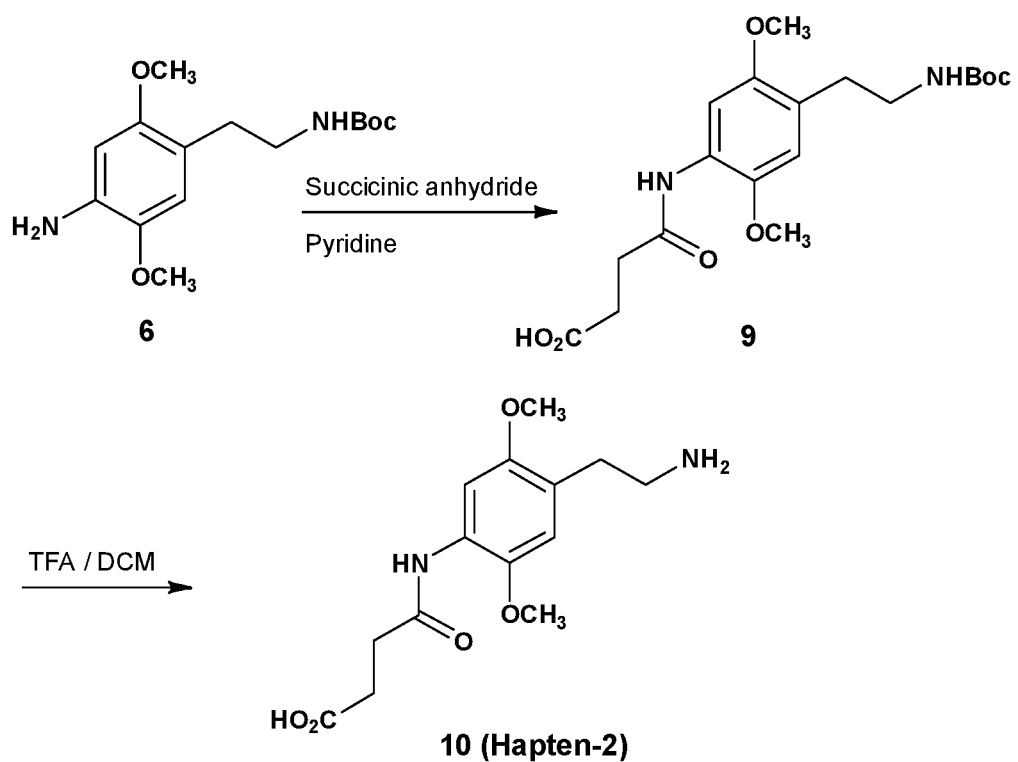
Figure 6:
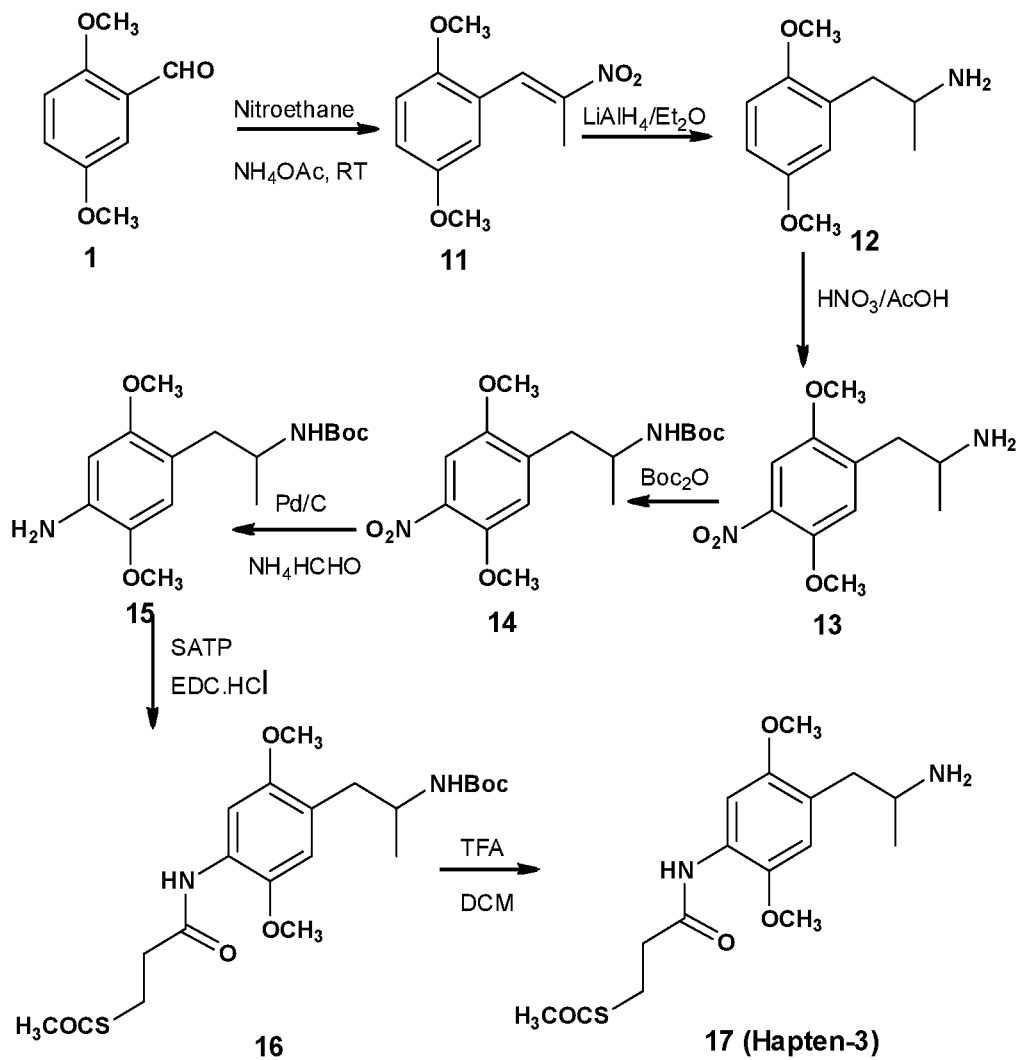
Figure 7:
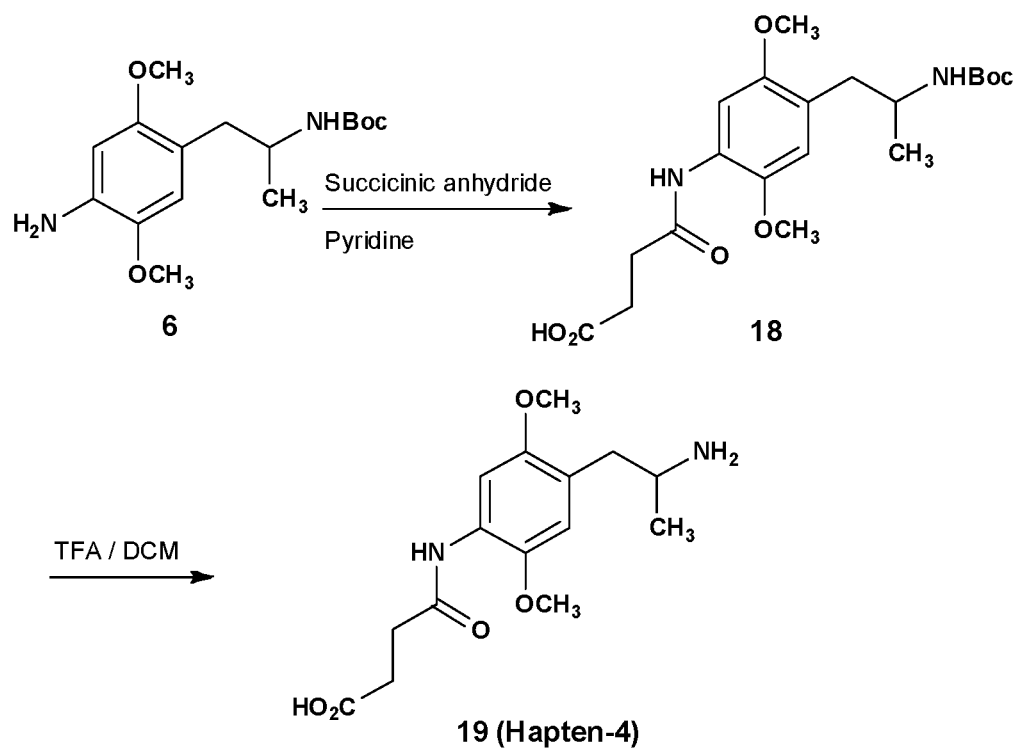

FIG. 1 Examples of compounds in various phenethylamine sub-families.
FIG. 2 Examples of members of the 2C and DO sub-families (with abbreviations).
FIG. 3 Exemplary haptens and immunogens.
FIG. 4 Synthesis of Hapten-1.
FIG. 5 Synthesis of Hapten-2.
FIG. 6 Synthesis of Hapten-3.
FIG. 7 Synthesis of Hapten-4.

SUMMARY OF THE INVENTION

Described herein are the first known immunoassays for the selective detection and determination of phenethylamines of the 2C and DO sub-families. The immunoassays are underpinned by novel, sensitive, sub-family-specific antibodies. The invention further describes substrates comprising an antibody specific to compounds of the 2C sub-family and/or an antibody specific to compounds of the DO sub-family. Also described are novel immunogens and kits incorporating antibodies of the invention.

DETAILED DESCRIPTION OF THE INVENTION

A first aspect of the invention is an immunoassay method of detecting or determining (determining is synonymous with quantifying) phenethylamines of the 2C sub-family, the DO sub-family or both the 2C and DO sub-families. The method comprises contacting an in vitro sample taken from an individual or a solution with an antibody specific to phenethylamines of the 2C sub-family but that does not cross-react with phenethylamines of the DO sub-family and/or an antibody specific to phenethylamines of the DO sub-family but that does not cross-react with phenethylamines of the 2C sub-family; and one or more detecting agents; measuring the signal produced by the detecting agent; and deducing from a calibration curve the presence of, or amount of, phenethylamines of the sub-family 2C, the sub-family DO or both the 2C and DO sub-families.

The in vitro sample is any suitable biological sample such as, but not limited to, blood, serum, plasma, urine or saliva. The in vitro sample is preferably a serum, plasma or urine sample.

The solution can be a liquid suspected of containing one or more of these drugs. Alternatively, as drugs of the 2C and DO families are often in tablet form, analysis of drugs suspected of containing these psychoactive ingredients may require pre-treatment to achieve a formulation suitable for immunoanalysis, such as dissolution in a suitable liquid.

The immunoassay method is based on the well-known competitive assay format in which a target analyte which binds to the antibody i.e. the molecule to be detected or determined, competes with a detecting agent which also binds to the antibody, for binding sites on the antibody; the more analyte present, the less detecting agent that binds to the antibody and the lower the measured signal.

The detecting agent can be any detectable substance such as an enzyme, a substance having fluorescent properties or a radioactive label; it is usual for an immunoassay that the detecting agent is a structure similar to the target analyte in which an enzyme or a substance having fluorescent properties has been conjugated, or in which a radiolabel has been incorporated. Conjugation is by way of standard methods familiar to the skilled person. Preferably, for the immunoassay method of the invention, the detecting agent is based on a compound with a phenethylamine substructure conjugated to an enzyme or fluorescent molecule. Examples of detecting agents and their syntheses are described the General Methods, Examples and Results section.

The 'detecting and determining' criteria for the immunoassay method includes, as is well-known in the art, exceeding a pre-defined cut-off/concentration value or measuring the calibrator equivalent value as derived from a calibrator curve (also referred to as a standard curve).

In a preferred embodiment, the antibody specific to phenethylamines of the 2C sub-family but that does not cross-react with phenethylamines of the DO sub-family is derived from an immunogen derivatised through the 4-position of 2,5-dimethoxyphenethylamine and the antibody specific to phenethylamines of the DO sub-family but that does not cross-react with phenethylamines of the 2C sub-family is derived from an immunogen derivatised through the 4-position of 2,5-dimethoxy-N-methylphenethylamine.

The antibody specific to phenethylamines of the 2C sub-family but that does not cross-react with phenethylamines of the DO sub-family is derived from an immunogen of structure I in which Q is H and the antibody specific to phenethylamines of the DO sub-family but that does not cross-react with phenethylamines of the 2C sub-family is derived from an immunogen of structure I in which Q is CHs

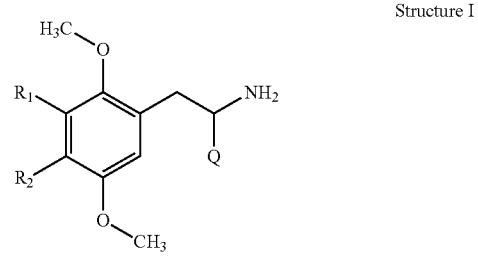

Structure I

For Structure I (whether Q is H or $CH_3$), one of $R_1$ and R2 is H and the other is

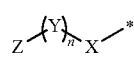

where X is $-(alk)_{n1}(A)_{n2}-$ in which A, which is attached to the phenethylamine moiety, is O, S, or —N(H)—, alk is $C_{1-6}$, substituted or unsubstituted straight chain alkylene or arylene moiety and n1 and n2 are independently 0 or 1; Y is a crosslinking group, n=0 or 1; and Z is an antigenicity conferring carrier material (accm). Optionally, alk is 01-6, substituted straight chain alkylene moiety, wherein the alkylene moiety is terminally substituted at each end. Further optionally, the, or each terminal substitution is selected from a bivalent heteroatom such as S or a carbonyl moiety (C=O). Preferably $R_1$ is H. When n1 and n2 are both 0, X is absent.

In a preferred embodiment the antibody used in the method of the invention to detect phenethylamines of the DO sub-family is derived from an immunogen of Structure I in which $R_1$ is H, Q is CHs, n1 and n2=1, A is —N(H)—, alk is —S—CH$_2$—CH$_2$—CO—, Y is 4-(succinimido-N-methyl)cyclohexylcarbonyl, Z is BSA. To detect phenethylamines of the 2C sub-family, the antibody is preferably derived from an immunogen of Structure I in which $R_1$ is H, Q is H, n1 and n2=1, A is —N(H)—, alk is —S—CH$_2$—CH$_2$—CO—, Y is 4-(succinimido-N-methyl)cyclohexylcarbonyl and Z is BSA (Immunogen of FIG. 3).

Optionally, the antibody specific to phenethylamines of the DO sub-family shows a cross-reactivity of less than 5%, further optionally, less than 1% for dimethylamylamine, when compared to 100% for DOB. It will be appreciated that the anorectic dimethylamylamine has been shown to cross-react with amphetamine immunoassays (Vorce et al 2011) and that it is desirable that avoidance of a false positive, by the presence of dimethylamylamine, is desirable.

Alternatively or additionally, optionally, the antibody specific to phenethylamines of the DO sub-family shows a cross-reactivity of less than 5%, further optionally, less than 1% for one or both of amphetamine and methamphetamine, when compared to 100% for DOB. It will be appreciated that avoidance of a false positive, by the presence of amphetamine and/or methamphetamine, is desirable when it is desired to detect drugs of the DO sub-family.

Alternatively or additionally, optionally, the antibody specific to phenethylamines of the DO sub-family shows a cross-reactivity of less than 5%, further optionally, less than 1% for 2C-B, when compared to 100% for DOB. It will be appreciated that DOB and 2C-B differ only in the presence or absence of a methyl side chain adjacent the amino group. It will also be appreciated that the absence of cross-reactivity between DOB and 2C-B facilitates detection of, and discrimination between, drugs of the DO and 2C sub-families.

Alternatively or additionally, optionally, the antibody specific to phenethylamines of the DO sub-family are considerably more sensitive to the DO sub-family than the assays tested in Petrie et al (2013). Optionally, the antibody specific to phenethylamines of the DO sub-family shows a sensitivity ($IC_{50}$) of less than 100 ng/mL, further optionally, less than 25 ng/mL, still further optionally, less than 10, or less than 5, or less than 2.5, ng/mL for DOB.

The antibody specific to phenethylamines of the DO sub-family may exhibit any one, any two, any three or all four, of the above-mentioned four properties.

Optionally, the antibody specific to phenethylamines of the 2C sub-family shows a cross-reactivity of less than 5%, further optionally, less than 1% for dimethylamylamine, when compared to 100% for 2C-B. It will be appreciated that the anorectic dimethylamylamine has been shown to cross-react with amphetamine immunoassays (Vorce et al 2011) and that it is desirable that avoidance of a false positive, by the presence of dimethylamylamine, is desirable.

Alternatively or additionally, optionally, the antibody specific to phenethylamines of the 2C sub-family shows a cross-reactivity of less than 5%, further optionally, less than 1% for one or both of amphetamine and methamphetamine, when compared to 100% for 2C-B. It will be appreciated that avoidance of a false positive, by the presence of amphetamine and/or methamphetamine, is desirable when it is desired to detect drugs of the 2C sub-family.

Alternatively or additionally, optionally, the antibody specific to phenethylamines of the 2C sub-family shows a cross-reactivity of less than 5%, further optionally, less than 1% for DOB, when compared to 100% for 2C-B. It will be appreciated that DOB and 2C-B differ only in the presence or absence of a methyl side chain adjacent the amino group. It will also be appreciated that the absence of cross-reactivity between DOB and 2C-B facilitates detection of, and discrimination between, drugs of the DO and 2C sub-families.

Alternatively or additionally, optionally, the antibody specific to phenethylamines of the 2C sub-family are considerably more sensitive to the 2C sub-family than the assays tested in Petrie et al (2013). Optionally, the antibody specific to phenethylamines of the 2C sub-family shows a sensitivity ($IC_{50}$) of less than 100 ng/mL, further optionally, less than 25 ng/mL, for DOB.

The antibody specific to phenethylamines of the 2C sub-family may exhibit any one, any two, any three or all four, of the above-mentioned four properties.

Before conjugation to the antigenicity conferring carrier material, a preferred hapten is Hapten-1 (FIG. 3).

Antigenicity conferring carrier materials and crosslinking groups in relation to small molecules and Structure I. Antigenicity conferring carrier materials are well known in the art and can be any material that makes all or part of the hapten (the pre-immunogenic molecule or 'small molecule') immunogenic, such as a protein, a protein fragment, a synthetic polypeptide or a semi-synthetic polypeptide.

The process of immunogen formation generally involves coupling of a hapten to a crosslinking agent, the latter subsequently coupled to an accm. It is also possible to couple a hapten directly to the accm. The concept of accm-(crosslinker)-hapten conjugation to form an immunogen is well-established; the conjugation and exact point of attachment of a hapten to a crosslinker must be adapted to the particular hapten and is guided by synthetic organic chemistry and immunology principles. The structure below highlights the components of an immunogen (in which n=0 or 1) based on a 2,5-dimethoxyphenethylamine hapten substituted at the 4-position; the hapten could equally be substituted at the 3-position, or a 2,5-dimethoxy-N-methyl-phenethylamine hapten substituted at the 3- or 4-position.

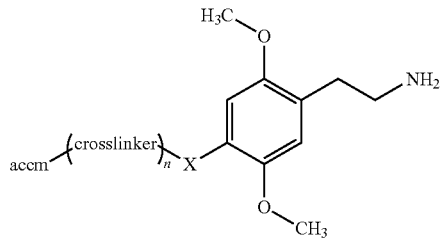

The X group is chosen from a heteroatom such as N, O or S; a short chain saturated, substituted or unsubstituted alkyl chain of 1-6 carbon atoms functionalised at the chain end; an arylene group optionally functionalised; a heteroatom coupled either to a saturated alkyl linear chain of 1-6 carbon atoms functionalised at the chain end or to an arylene group optionally functionalised. The chain-end or arylene functionalisation enables coupling to either the crosslinker or directly to the accm; optionally, the arylene can be coupled directly to the crosslinker. The total linear chain length of X or X plus crosslinker is preferably 1-10 atoms (in the context of the current invention for ease of interpretation of the phrase 'total linear chain length', a ring system in X or the crosslinker corresponds to one atom i.e. a benzene ring in X and a cyclohexane ring in the crosslinker corresponds to 2 atoms). Numerous crosslinkers and accms are commercially available and have been described in the literature (Thermo Scientific Crosslinking Technical Handbook, 1606073 04/2009; Bioconjugate Techniques G. Hermanson, ed, Academic Press, 1996, 785 pp—lists common carrier proteins). An example of a crosslinking group is 4-N-maleimidomethylcyclohexyl-1-carboxylic acid NHS ester solution (available from Sigma-Aldrich catalogue number 5525). An alternative crosslinker which can used to couple to haptens possessing a carboxylic acid, as exemplified by Haptens-2 and -4, is EDC and sulfo-NHS, both of which are known in the art and are commercially available.

A further aspect of the invention is antibodies that specifically bind to an epitope incorporated in, or within or overlapping, or of phenethylamines of the 2C sub-family; by definition these antibodies do not cross-react with phenethylamines of the DO sub-family. This epitope is defined by Structure II, i.e., the epitope bound by the antibody is defined by the benzene ring, the two methoxy groups and the ethylamine moiety.

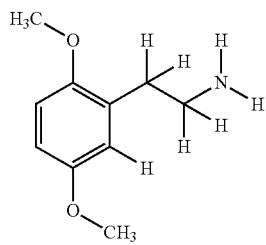

Structure II

The 2C sub-family antibodies are further characterized by the immunogen from which they are derived (in the context of the current invention, 'from which they are derived' is synonymous with 'to which they are raised'), and by their cross-reactivity pattern in which the antibodies are specific to phenethylamines of the 2C sub-family and have no cross-reactivity to phenethylamines of the DO sub-family. By the term "no cross-reactivity" is meant <1% cross-reactivity to DOB and, optionally, <1% cross-reactivity to one or both of (+)-phenethylamine and dimethylamylamine. Alternatively or additionally, a 2C sub-family antibody might exhibit an $IC_{50}$ of more than 20 ng/ml for 2C-B.

Another aspect of the invention is antibodies that specifically bind to an epitope incorporated in, or within or overlapping or of phenethylamines of the DO sub-family; by definition these antibodies do not cross-react with phenethylamines of the 2C sub-family. This epitope is defined by Structure III, i.e., the epitope bound by the antibody is defined by the benzene ring, the two methoxy groups and the propan-2-amine moiety.

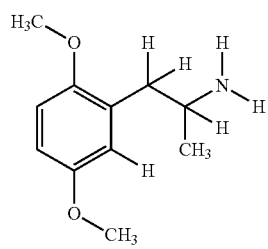

Structure III

This includes phenethylamines of the DO sub-family, as illustrated below (Bromo DragonFly), in which each methoxy group is fused to the phenyl ring through a methylene group (forming a fused furan ring). The above-mentioned phenethylamines of the 2C sub-family also include compounds in which each methoxy group is fused to the phenyl ring through a methylene group (also forming a fused furan ring—not illustrated):

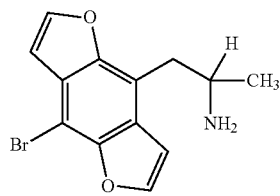 [SMILES: CC(N)Cc1c2ccoc2c(Br)c2ccoc12]

The DO sub-family antibodies are further characterized by the immunogen from which they are derived and by their cross-reactivity pattern, in which the antibodies cross-react with phenethylamines of the DO sub-family and have no cross-reactivity to phenethylamines of the 2C sub-family. By the term "no cross-reactivity" is meant <1% cross-reactivity to 1-(4-bromo-2,5-dimethoxyphenyl)ethan-2-amine (2C-B) and, optionally, <1% cross-reactivity to one or more of 1-(2,5-dimethoxy-4-propylphenyl)ethan-2-amine (2C-P), 1-(2,5-dimethoxy-4-ethylphenyl)ethan-2-amine (2C-E), 1-(2,5-dimethoxy-4-ethylthiophenyl)ethan-2-amine (2C-T2), 1-(4-chloro-2,5-dimethoxyphenyl)ethan-2-amine (2C-C), 1-(2,5-dimethoxy-4-propylthiophenyl)ethan-2-amine (2C-T-7), 1-(2,5-dimethoxy4-methylphenyl)ethan-2-amine (2C-D) and 1-(4-cyano-2,5-dimethoxyphenyl)ethan-2-amine (2C-CN) and, further optionally, <1% cross-reactivity to one or more of dimethylamylamine, methamphetamine. amphetamine and amphetamine. Alternatively or additionally, a DO sub-family antibody might exhibit an $IC_{50}$ of more than 2 ng/ml for DOB.

Explicit hydrogen atoms within each of Structure II and Structure III indicate that no further molecular substitution is possible at the atoms to which these explicit hydrogen atoms are attached. Structures IV (2C sub-family) and V (DO sub-family) are representative molecules to which the epitope-specific antibodies of the invention bind:

Structure IV

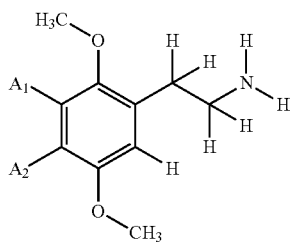

Structure V

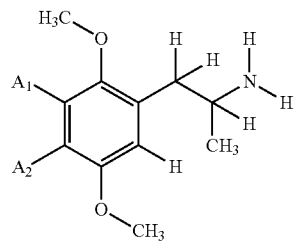

wherein one of $A_1$ and $A_2$ is H and the other is $NO_2$, Cl, BR, F, I, $CH_3$, $CH_3$—O—, $CH_3$—$CH_2$—, $CH_3$—$CH_2$—$CH_2$—, $CH_3$—$CH_2$—S—, $(CH_3)_2$—CH—S—, $CH_3$—$CH_2$—$CH_2$—S—, $CH_3$—$CH_2$—$CH_2$—$CH_2$—S—, $(CH_3)_3$—C—S— or F—$CH_2$—$CH_2$—S—, or both $A_1$ and $A_2$ are H; or $A_1$ and $A_2$ together with the existing benzene ring form a benzo[1,3]dioxane ring system.

Due to inter-molecular attractive forces such as hydrogen bonding and van der Waal's forces, there is often a degree of binding or affinity between two molecules whatever their respective structures; the skilled person recognizes that no cross-reactivity or minimal cross-reactivity implies that, in the context of a working immunoassay, any binding or interaction between an antibody and non-target analytes is at such a low level that it does not compromise the integrity of the immunoassay, i.e., false positives are avoided.

Molecules present in solutions or in vitro biological samples which show cross-reactivity towards the antibody can be detected by immunoassays incorporating said antibodies; such molecules are detectable at 100 ng/ml, preferably 50 ng/ml, more preferably 5 ng/ml.

Examples of members of the relevant phenethylamine sub-families, with which the antibodies of the invention cross-react, are depicted in FIG. 2.

Antibodies specific to an epitope of the DO sub-family are further characterised by being derived from an immunogen of Structure VI Structure VI

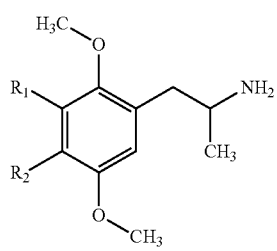

wherein one of $R_1$ and $R_2$ is H and the other is

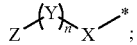

X is $-(alk)_{n1}-(A)_{n2}-$ in which A is O, S, or —N(H)—, alk is $C_{1-6}$, substituted or unsubstituted straight chain alkylene or arylene moiety and n1 and n2 are independently 0 or 1; Y is a crosslinking group and n=0 or 1; Z is an accm. The crosslinking group and the accm of Structure VI are as previously described for Structure I. In a preferred embodiment, $R_1$ is H.

Antibodies specific to molecules of the 2C sub-family are further characterised by being derived from an immunogen of Structure VII Structure VII

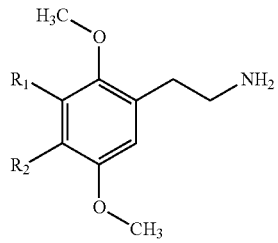

wherein one of $R_1$ and $R_2$ is H and the other is

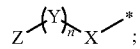

X is $-(alk)_{n1}(A)_{n2}-$ in which A is O, S, or —N(H)—, alk is $C_{1-6}$, substituted or unsubstituted straight chain alkylene or arylene moiety and n1 and n2 are independently 0 or 1; Y is a crosslinking group and n=0 or 1; Z is an accm. The crosslinking group and the accm of Structure VII are as previously described for Structure I. In a preferred embodiment, $R_1$ is H.

The invention also describes immunogens of Structures VI and VII where X is $-(alk)_{n1}-(A)_{n2}-$ in which A is O, S, or —N(H)—, alk is $C_{1-6}$, substituted or unsubstituted straight chain alkylene or arylene moiety and n1 and n2 are independently 0 or 1; Y is a crosslinking group and n=0 or 1; Z is an accm. The crosslinking group and the accm of Structures VI and VII are as previously described for Structure I.

The invention further describes a substrate with which the antibodies of the invention engage. The antibodies can engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated) but is, preferably, of a planar conformation (optionally chemically-activated) such as a biochip.

A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate prior to antibody placement. Either the upper surface, or both surfaces, of the substrate can be coated. As the antibodies of the invention are selectively specific to either the 2C or DO sub-families, two or more sets of antibodies can be placed on the same planar substrate at discrete locations (so-called 'spatially addressable locations'). An immunoassay incorporating the antibodies of the invention on a single substrate enables the proficient screening of biological, product and environmental samples by highlighting not only the presence of any phenethylamines of the 2C and DO sub-families in the sample, but also to which sub-family the phenethylamine(s) belong(s); this makes the subsequent mass-spectrometric confirmatory step, if required, less analytically complex. Other compound-specific or compound generic antibodies can also be incorporated onto the substrate, such as antibodies cross-reactive to methamphetamine, amphetamine and/or MDMA.

General Methods, Examples and Results

Preparation of Haptens, Immunogens and Detecting Agents

In immunology, haptens are defined as chemicals which by themselves cannot elicit immune responses; they require chemical coupling to larger immunogenic molecules (antigenicity conferring carrier materials/molecules or 'accm'), to be capable of inducing an immune response.

Appropriate accms commonly contain poly(amino acid) segments and include polypeptides, proteins and protein fragments. Illustrative examples of antigencity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

Conjugation of haptens can be performed using standard methods of conjugation such as mixed anhydride, EDC or succinimidyl activation of the haptens. In order to confirm that adequate conjugation of hapten to carrier material has been achieved, prior to immunisation, each immunogen is evaluated using matrix-assisted UV laser desorption/onisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluke) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilized on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Example 1: Preparation of (E)-1,4-dimethoxy-2-(2-nitrovinyl)benzene 2

2,5-Dimethoxy benzaldehyde 1 (15 g, 0.09 mol) was dissolved in nitromethane (60 ml) and ammonium acetate (6.96 g, 0.09 mol) was added at room temperature. The resulting mixture was refluxed for 5 hours, then left stirring at room temperature over the weekend. The solvent was evaporated in vacuo, the residue was taken up in dichloromethane and washed 2 times with water, 4 times with 3M HCl and once with brine. The organic portion was then dried over sodium sulfate, filtered and concentrated in vacuo to give 30 g crude brown/red solid. The residue was purified by column chromatography (Silica gel, 5-30% dichloromethane in hexane) to give 9.87 g of (E)-1,4-dimethoxy-2-(2-nitrovinyl)benzene 2 as a light orange solid.

Example 2: Preparation of 2-(2,5-dimethoxyphenyl)ethanamine 3

Lithium aluminum hydride (LAlH$_4$) (5.38 g, 0.14 mol) was added portion-wise to anhydrous tetrahydrofuran (250 ml) and then (E)-1,4-dimethoxy-2-(2-nitrovinyl) benzene 2 (9.87 g, 0.047 mol) dissolved in anhydrous tetrahydrofuran (150 ml) was added drop-wise. The reaction mixture was refluxed for 4 hours then stirred at room temperature overnight. To quench the reaction mixture, water (5 ml) followed by 1 M sodium hydroxide (5 ml) and then water (15 ml) were added slowly while cooling. The resulting mixture was then stirred at room temperature and the white precipitate which formed was removed by filtration through a celite plug and washed with $Et_2O$. The solvent was removed under vacuo to give 5.76 g of 2-(2,5-dimethoxyphenyl) ethanamine 3 crude as yellow oil.

Example 3: Preparation of 2-(2,5-dimethoxy-4-nitrophenyl)ethanamine 4

2-(2,5-Dimethoxyphenyl) ethanamine 3 (5.76 g, 31.78 mmol) was dissolved in a mixture of acetic acid (115 ml) and nitric acid (19 ml) with cooling at 0° C. The reaction mixture was stirred for 1 hour at 0° C. The reaction mixture was poured over a mixture of water and ice and 6 M sodium hydroxide was used to bring the pH to alkaline. Then the solution was extracted with a mixture of (1/1) benzene/ether. The organic layer was dried over sodium sulfate, filtered and was evaporated to dryness to give 6.16 g of 2-(2,5-dimethoxy-4-nitrophenyl) ethanamine 4 as dark brown crude oil used in the next step without any further purification.

Example 4: Preparation of tert-butyl 2,5-dimethoxy-4-nitrophenethylcarbamate 5

2-(2,5-dimethoxy-4-nitrophenyl) ethanamine 4 (6.16 g, 27 mmol) was dissolved in dichloromethane (40 ml) and triethylamine (7.52 ml, 54 mmol) was added followed by di-tert-butyl dicarbonate (8.91 g, 40.8 mmol). The reaction mixture was stirred at room temperature over the weekend. The reaction mixture was washed with brine and dried over sodium sulfate and the solvent was removed under vacuo. The residue was purified by column chromatography (silica gel, 0-30% ethyl acetate in hexane containing 5% chloroform) to give 2 g of tert-butyl 2,5-dimethoxy-4-nitrophenethylcarbamate 5 as a brown oil that solidified with time.

Example 5: Preparation of tert-butyl 2,5-dimethoxy-4-aminophenethtlcarbamate 6

Tert-Butyl 2,5-dimethoxy-4-nitrophenethylcarbamate 5 (1.77 g, 7.8 mmol) was dissolved in methanol (100 ml) and tetrahydrofuran (10 ml). Ammonium formate (2.67 g, 0.042 mol) was added followed, cautiously, by 5% Pd/C (460 mg). The reaction mixture was stirred at room temperature for one hour. The reaction mixture was filtered on a celite plug and the solvent was removed under vacuo. The residue was purified by column chromatography (silica gel, 0-50% ethyl acetate in hexane) to give 1.19 g of tert-butyl 2,5-dimethoxy-4-aminophenethylcarbamate 6 as a pink solid.

Example 6: Preparation of S-(3-((4-(2-((tert-butoxycarbonyl)amino)ethyl)-2,5-dimethoxyphenyl) amino)-3-oxopropyl) Ethanethiate 7

3-Acetylthiopropionic acid (210 mg, 1.4 mmol) was dissolved in pyridine (3 ml) then N-(3-dimethylaminopropyl)-N'-ethylcarbodiimide hydrochloride (EDC. HCl) (324 mg, 1.69 mmol) and N, N-dimethylaminopyridine (DMAP) (51 mg, 0.42 mmol) were added followed by tert-butyl 2,5-dimethoxy-4-aminophenethylcarbamate 6 (500 mg, 1.69 mmol). The reaction mixture was stirred at room temperature over the weekend. The solvent was removed under vacuo and the residue was taken up in water and ethyl acetate. The layers were separated and the aqueous layer was extracted 3 more times with ethyl acetate. The combined organic layers were washed with brine, dried over sodium sulfate, filtered and evaporated to dryness. The residue was purified by column chromatography (silica gel, 0-50% ethyl acetate in hexane) to give 475 mg of S-(3-((4-(2-((tert-butoxycarbonyl) amino) ethyl)-2,5-dimethoxyphenyl) amino)-3-oxopropyl) ethanethioate 7 as a white solid.

Example 7: Preparation of S-(3-((4-(2-aminoethyl)-2,5-dimethoxyphenyl)amino)-3-oxopropyl) Ethanethioate 8 (Hapten 1)

S-(3-((4-(2-((tert-butoxycarbonyl) amino) ethyl)-2,5-dimethoxyphenyl) amino)-3-oxopropyl) ethanethioate 7 (475 mg, 1.45 mmol) was dissolved in dichloromethane (5 ml) and trifluoroacetic acid (5 ml) was added drop-wise at 0° C. The reaction mixture was left to warm up at room temperature and then stirred overnight. The solvent was removed under vacuo. The residue was purified by column chromatography (silica gel, 0-30% methanol in chloroform) to give 400 mg of S-(3-((4-(2-aminoethyl)-2,5-dimethoxyphenyl) amino)-3-oxopropyl) ethanethioate 8 (hapten-1) as a brown oil.

Example 8: Preparation of 4-((4(4-(2-((tert-butoxycarbonyl)amino)ethyl)-2,5-dimethoxyphenyl) amino)-4-oxobutanoic Acid 9

Tert-Butyl 2,5-dimethoxy-4-aminophenethylcarbamate 6 (1 g, 3.37 mmol) was dissolved in pyridine (10 ml). Succinic anhydride (1.69 g, 16 mmol) and triethylamine (2 ml) were added and the reaction mixture was stirred overnight at room temperature. The solvent was removed under vacuo and the residue was taken into ethyl acetate and 1M HCl, after separation the aqueous layer was extracted with ethyl acetate. The organic layers were combined, washed with brine, dried over sodium sulfate and filtered. The solvent was evaporated and the residue was purified by column chromatography (silica gel, 0-30% methanol in chloroform) to give 740 mg of 4-((4-(2-((tert-butoxycarbonyl) amino) ethyl)-2,5-dimethoxyphenyl)amino)-4-oxobutanoic acid 9 as a white solid.

Example 9: Preparation of (2,5-dimethoxy-4-succinamido) Amphetamine 10 (Hapten 2)

4-((4-(2-((tert-butoxycarbonyl) amino) ethyl)-2,5-dimethoxyphenyl) amino)-4-oxobutanoic acid 9 (500 mg, 1.68 mmol) was dissolved in dichloromethane (5 ml) and trifluoroacetic acid (5 ml) was added drop-wise at 0° C. The reaction mixture was left to warm up at room temperature and then stirred overnight. The solvent was removed under vacuo. The residue was purified by column chromatography (silica gel, 0-30% methanol in chloroform) to give 410 mg of (2,5-dimethoxy-4-succinamido) amphetamine 10 (hapten-2) as a brown oil.

Example 10: Conjugation S-(3-((4(4-(2-aminoethyl)-2,5-dimethoxyphenyl) Amino)-3-oxopropyl) Ethanethioate 8 to BSA 4-N-Maleimidomethylcyclohexyl-1-carboxylic acid NHS ester (55.3 mg) in N,N-Dimethylformamide (0.6 mL) was added drop-wise to Albumin from bovine serum (200 mg) dissolved in 50 mM HEPES solution, pH8.5 (20 mL) while stirring. The resulting solution was stirred at 15-25° C. for 40 minutes. Excess 4-N-Maleimidomethylcyclohexyl-1-carboxylic acid NHS ester was removed by dialysis against Phosphate Buffered Saline, pH 7.2. The acetyl S-(3-((4-(2-aminoethyl)-2,5-dimethoxyphenyl) amino)-3-oxopropyl) ethanethioate 8 (hapten-1) (37.8 mg) was dissolved in N,N-Dimethylformamide (3.78 mL). 3.78 mL of 1M Potassium hydroxide solution was added to the above hapten solution while stirring during 10 minutes period. Then 9.45 mL of 0.2 M Phosphate buffer, pH7.0 was added to quench reaction; 2.835 mL of 1 M HCl solution was added to bring pH to 7.0. The modified carrier protein was added to the activated hapten, rolled for 2 hours at +15-+25° C., and then transferred to +2-+8° C. and rolled for 16-20 hours. Excess hapten was removed by dialysis at 2-8° C. against Phosphate Buffered Saline, pH 7.2.

Example 11: Conjugation S-(3-((4(4-(2-amino-ethyl)-2,5-dimethoxyphenyl) amino)-3-oxopropyl) ethanethioate 8 to HRP 4-N-Maleimidomethylcyclohexyl-1-carboxylic acid NHS ester (0.84 mg) in N,N-Dimethylformamide (0.045 mL) was added drop-wise to HRP (20 mg) dissolved in 50 mM HEPES solution, pH8.5 (0.8 mL) while stirring, protected from light. The resulting solution was stirred at 15-25° C. for 40 minutes. Excess 4-N-Maleimidomethylcyclohexyl-1-carboxylic acid NHS ester was removed by dialysis against Phosphate Buffered Saline, pH 7.2. The solution was protected from light during the process. The S-(3-((4-(2-amino-ethyl)-2,5-dimethoxyphenyl) amino)-3-oxopropyl) ethanethioate 8 (hapten-1) (2 mg) was dissolved in N,N-Dimethylformamide (0.2 mL). 0.2 mL of 1 M Potassium hydroxide solution was added to the above hapten solution while stirring during 10 minutes period. Then 0.5 mL of 0.2 M Phosphate buffer, pH7.0 was added to quench reaction; 0.15 mL of 1 M HCl solution was added to bring pH to 7.0. The modified HRP was added to the activated hapten, rolled for 2 hours at +15-+25° C., and then transferred to +2-+8° C. and rolled for 16-20 hours. Excess hapten was removed with PD-10 column (Pharmacia), pre-equilibrated with Phosphate Buffered Saline, pH 7.2, followed by dialysis at 2-8° C. against Phosphate Buffered Saline, pH 7.2.

Example 12: Preparation of (E)-1,4-dimethoxy-2-(2-nitroprop-1-en-1-yl)benzene 11

2,5-Dimethoxybenzaldehyde 1 (15 g, 0.09 mol) was dissolved in nitroethane (60 ml) and ammonium acetate (6.96 g, 0.09 mol) was added at room temperature. The resulting mixture was refluxed for 5 hours, then left stirring at room temperature overnight. The solvent was evaporated under reduced pressure, the residue was taken up in dichloromethane and washed 2 times with water, 4 times with 3 M HCl and once with brine. The organic layer was dried over sodium sulfate, filtered and evaporated to dryness to give 21.8 g of a crude brown solid. The residue was purified by column chromatography (silica gel, 5-30% dichloromethane in hexane) to give 14.35 g of (E)-1,4-dimethoxy-2-(2-nitroprop-1-en-1-yl)benzene 11 as a light yellow solid.

Example 13: Preparation of 1-(2,5-dimethoxyphenyl) propan-2-amine 12

Lithium aluminum hydride (7.15 g, 0.19 mol) was added portion-wise to anhydrous tetrahydrofuran (300 ml) and then (E)-1,4-dimethoxy-2-(2-nitroprop-1-en-1-yl) benzene 11 (14 g, 0.063 mol) dissolved in anhydrous tetrahydrofuran (200 ml) was added drop-wise. The reaction mixture was refluxed overnight. To quench the reaction mixture, water (7 ml) followed by 1 M sodium hydroxide (7 ml) and then water (21 ml) were added slowly with cooling. The resulting mixture was stirred at room temperature until the formation of white precipitate then filtered on celite plug and washed with diethylether. The solvent was removed under vacuo to give the 1-(2,5-dimethoxyphenyl) propan-2-amine (12.31 g) 12 crude as yellow oil.

Example 14: Preparation of 1-(2,5-dimethoxy-4-nitrophenyl) propan-2-amine 13

Crude 1-(2,5-dimethoxyphenyl) propan-2-amine 12 (12.3 g) was dissolved in acetic acid (62 ml). To this solution was added at 0° C. 50% aqueous nitric acid (66.5 ml) over a period of 30 minutes. The reaction mixture was stirred for 30 minutes at 0° C. The reaction mixture was poured over ice/water mixture and 6 M sodium hydroxide was used to bring the pH to alkaline. Then the solution was extracted with a mixture of 1/1 benzene/ether, the organic layer was dried over sodium sulfate and the solvent was evaporated to give 14 g of 1-(2,5-dimethoxy-4-nitrophenyl) propan-2-amine 13 as crude oil.

Example 15: Preparation of tert-butyl (1-(2,5-dimethoxy-4-nitrophenyl) propan-2-yl) Carbamate 14

Crude 1-(2,5-dimethoxy-4-nitrophenyl) propan-2-amine 13 (14 g) was dissolved in dichloromethane (125 ml) and triethylamine (16.16 ml, 116 mmol) was added followed by di-tert-butyl dicarbonate (19.1 g, 87 mmol). The reaction mixture was stirred at room temperature over the weekend. The reaction mixture was washed with brine, dried over sodium sulfate, filtered and evaporated to dryness. The residue was purified by column chromatography (silica gel, 0-30% ethyl acetate in hexane containing 5% chloroform) to give 15.6 g of tert-butyl (1-(2,5-dimethoxy-4-nitrophenyl) propan-2-yl) carbamate 14 as a brown oil.

Example 16: Preparation of tert-butyl(1-(4-amino-2,5-dimethoxyphenyl)propan-2-yl)carbamate 15

Tert-Butyl (1-(2,5-dimethoxy-4-nitrophenyl)propan-2-yl) carbamate 14 (5 g, 14.6 mmol) was dissolved in methanol (100 ml). Ammonium formate (4.97 g, 0.078 mol) was added followed, cautiously, by 5% Pd/C (883 mg). The reaction mixture was stirred at room temperature for one hour. The reaction mixture was filtered on a celite plug and washed with dichloromethane. The solvent was removed under vacuo and the residue was purified by column chromatography (silica gel, 0-50% ethyl acetate in hexane) to give 3.12 g of tert-butyl (1-(4-amino-2,5-dimethoxyphenyl) propan-2-yl)carbamate 15 as an off white solid.

Example 17: Preparation of S-(3-((4-(2-((tert-butoxycarbonyl)amino) propyl)-2,5-dimethoxyphenyl) amino)-3-oxopropyl) Ethanethioate 16

3-Acetylthiopropionic acid (210 mg, 1.34 mmol) was dissolved in pyridine (3 ml), then N- (3-dimethylaminopropyl)-N'-ethylcarbodiimide hydrochloride EDC (308 mg, 1.61 mmol) and dimethylaminopyridine (DMAP) (50 mg, 0.4 mmol) were added followed by tert-butyl (1-(4-amino-2,5-dimethoxyphenyl)propan-2-yl)carbamate 15 (500 mg, 1.61 mmol). The reaction mixture was stirred at room temperature over the weekend. The solvent was removed under vacuo and the residue was taken up in water and ethyl acetate. The layers were separated and the aqueous layer was extracted 3 more times with ethyl acetate. The combined organic layers were washed with brine, dried over sodium sulfate, filtered and evaporated to dryness. The residue was purified by column chromatography (silica gel, 0-50% ethyl acetate in hexane) to give 480 mg of S-(3-((4-(2-((tert-butoxycarbonyl)amino)propyl)-2,5-dimethoxyphenyl)amino)-3-oxopropyl)ethanethioate 16 as a white solid.

Example 18: Preparation of S-(3-((4-(2-aminopropyl)-2, 5-dimethoxyphenyl)amino)-3-oxopropyl) Ethanethioate 17 (Hapten-3)

S-(3-((4-(2-((tert-butoxycarbonyl) amino) propyl)-2, 5-dimethoxyphenyl) amino)-3-oxopropyl) ethanethioate 16 (480 mg, 1.11 mmol) was dissolved in dichloromethane (10 ml) and trifluoroacetic acid (5 ml) was added dropwise at 0° C. The reaction mixture was left to warm up at room temperature and then stirred overnight. The solvent was removed under vacuo. The residue was purified by column chromatography (silica gel, 0-30% methanol in chloroform) to give 410 mg of S-(3-((4-(2-aminopropyl)-2,5-dimethoxyphenyl) amino)-3-oxopropyl) ethanethioate 17 (Hapten-3) as a brown oil.

Example 19: Preparation of 4-((4(4-(2-((tert-butoxycarbonyl)amino)propyl)-2,5-dimethoxyphenyl) amino)-4-oxobutanoic Acid 18

Tert-butyl (1-(4-amino-2,5-dimethoxyphenyl)propan-2-yl)carbamate 15 (1 g, 3.22 mmol) was dissolved in pyridine (10 ml) and succinic anhydride (1.6 g, 15.9 mmol) and triethylamine (2 ml) were added and the reaction mixture was stirred overnight. The solvent was removed under vacuo and the residue was taken into ethyl acetate and 1 M HCl, after separation the aqueous layer was extracted with ethyl acetate. The organic layers were combined, washed with brine and dried over sodium sulfate. The solvent was evaporated and the residue was purified by column chromatography (silica gel, 0-30% methanol in chloroform) to give 903 mg of 4-((4-(2-((tert-butoxycarbonyl)amino) propyl)-2,5-dimethoxyphenyl)amino)-4-oxobutanoic acid 18 as a white powder.

Example 20: Preparation of 2,5-dioxopyrrolidin-1-yl-4-((4-(2-((tert-butoxycarbonyl) amino) propyl)-2, 5-dimethoxyphenyl)amino)-4-oxobutanoate 19 (Hapten-4)

4-((4-(2-((tert-butoxycarbonyl)amino) propyl)-2,5-dimethoxyphenyl)amino)-4-oxobutanoic acid 18 (576 mg, 1.40 mmol) was dissolved in dichloromethane (10 ml) and trifluoroacetic acid (5 ml) was added dropwise at 0° C. The reaction mixture was left to warm up at room temperature and then stirred overnight. The solvent was removed under vacuo. The residue was purified by column chromatography (Silica gel, 0-30% methanol in chloroform) to give 495 mg of 2,5-dioxopyrrolidin-1-yl4-((4-(2-((tert-butoxycarbonyl) amino) propyl)-2,5-dimethoxyphenyl)amino)-4-oxobutanoate 19 (Hapten-4).

Example 21: Conjugation S-(3-((4-(2-aminopropyl)-2,5-dimethoxyphenyl) amino)-3-oxopropyl) Ethanethioate 17 to BSA 4-N-Maleimidomethylcyclohexyl-1-carboxylic acid NHS ester (55.3 mg) in N,N-Dimethylformamide (0.6 mL) was added drop-wise to Albumin from bovine serum (200 mg) dissolved in 50 mM HEPES solution, pH8.5 (20 mL) while stirring. The resulting solution was stirred at 15-25° C. for 40 minutes. Excess 4-N-Maleimidomethylcyclohexyl-1-carboxylic acid NHS ester was removed by dialysis against Phosphate Buffered Saline, pH 7.2.

The acetyl S-(3-((4-(2-aminopropyl)-2,5-dimethoxyphenyl) amino)-3-oxopropyl) ethanethioate 17 (Hapten-3) (37.8 mg) was dissolved in N,N-Dimethylformamide (3.78 mL). 3.78 mL of 1 M Potassium hydroxide solution was added to the above hapten solution while stirring during 10 minutes period. Then 9.45 mL of 0.2 M Phosphate buffer, pH7.0 was added to quench reaction; 2.835 mL of 1 M HCl solution was added to bring pH to 7.0. The modified carrier protein was added to the activated hapten, rolled for 2 hours at +15-+25° C., and then transferred to +2-+8° C. rolled for 16-20 hours. Excess hapten was removed by dialysis at 2-8° C. against Phosphate Buffered Saline, pH 7.2.

DO antibodies 1 and 2 were raised against the immunogen of Example 21.

Example 22: Conjugation S- (3-((4-(2-aminopropyl)-2,5-dimethoxyphenyl) amino)-3-oxopropyl) ethanethioate 17 to HRP 4-N-Maleimidomethylcyclohexyl-1-carboxylic acid NHS ester solution (0.84 mg) in N, N-Dimethylformamide (0.045 mL) was added drop-wise to HRP (20 mg) dissolved in 50 mM HEPES solution, pH8.5 (0.8 mL) while stirring protected from light. Then the resulting solution was stirred at 15-25° C. for 40 minutes. Excess 4-N-Maleimidomethylcyclohexyl-1-carboxylic acid NHS ester was removed by dialysis against Phosphate Buffered Saline, pH 7.2. Keep the solution protected from light during the process. The acetyl S-(3-((4-(2-aminopropyl)-2,5-dimethoxyphenyl) amino)-3-oxopropyl) ethanethioate 17 (Hapten-3) (2 mg) was dissolved in N, N-Dimethylformamide (0.2 mL). 0.2 mL of 1 M Potassium hydroxide solution was added to the above hapten solution while stirring during 10 minutes period. Then 0.5 mL of 0.2 M Phosphate buffer, pH7.0 was added to quench reaction; 0.15 mL of 1 M HCl solution was added to bring pH to 7.0. The modified HRP was added to the activated hapten, roll for 2 hours at +15-+25° C., and then transfer to +2-+8° C. roll for 16-20 hours. Excess hapten was removed with PD-10 column (Pharmacia), pre-equilibrated with Phosphate Buffered Saline, pH 7.2, followed by dialysis at 2-8° C. against Phosphate Buffered Saline, pH 7.2.

Example 23: Immunoassay of 2C and DO Compounds and Selected Molecules a) Characterisation of Antibodies 1 and 2 to DOB-BSA It is currently understood that the more commonly encountered analogues of the DO sub-family are DOB, DOM, DOC and DOI, although this is likely to change over time.

The wells of an enhanced binding 96 well polystyrene microtitre plate were coated with IgG fraction of antiserum raised to DOB-BSA, diluted in 10 mM Tris, pH8.5 (125 µl/well). The appropriate antibody coating dilution was determined using standard ELISA checkerboard techniques. The plate was incubated for 2 hours at 37° C., washed 4 times over 10 minutes with Tris buffered saline containing Tween 20 (TBST) and tapped dry. Standard solutions of DOB were prepared in TBST at 0, 0.625, 1.25, 2.5, 5, 10, 20 & 40 ng/ml, and 50 µl of each was added to the appropriate wells. 75 µl of conjugate (Example 22) diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. Excess unbound conjugate was removed by washing 6 times over a 10-15 minute period with TBST and tapped dry. 125 µl of tetramethylbenzidine (TMB) substrate solution was added to each well of the plate that was then incubated for 20 minutes in the dark at room temperature. The reaction was terminated by addition of 125 µl 0.2 M $H_2SO_4$ to each well. The absorbance was measured at 450 nm using a microtitre plate reader. The data generated in the assay is presented in Table 1. In order to determine the specificity of the competitive ELISAs, standard solutions of a range of structurally similar compounds were prepared in TBST. Using calibration curves generated from these compounds (0-40 ng/ml), the cross-reactivity was determined.

The results of this study in relation to antibody 1 are presented in Tables 2 and 2a. The results of this study in relation to antibody 2 are presented in Table 2b.

b) Characterisation of Antibodies to 2C-B-BSA

It is currently understood that the more commonly encountered analogues of the 2C sub-family are 2C-I, 2C-B, 2C-C, 2C-D and 2C-E, although this is likely to change over time.

The wells of an enhanced binding 96 well polystyrene microtitre plate were coated with IgG fraction of antiserum raised to 2C-B-BSA, diluted in 10 mM Tris, pH8.5 (125 µl/well). The appropriate antibody coating dilution was determined using standard ELISA checkerboard techniques. The plate was incubated overnight at 4° C., washed 4 times over 10 minutes with Tris buffered saline containing Tween 20 (TBST) and tapped dry. Standard solutions of 2CB were prepared in TBST at 0, 1.25, 2.5, 5, 10, 20, 40 & 80 ng/ml, and 50 µl of each was added to the appropriate wells. 75 µl of conjugate (Example 11) diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. Excess unbound conjugate was removed by washing 6 times over a 10-15 minute period with TBST and tapped dry. 125 µl of tetramethylbenzidine (TMB) substrate solution was added to each well of the plate that was then incubated for 20 minutes in the dark at room temperature. The reaction was terminated by addition of 125 µl 0.2 M $H_2SO_4$ to each well. The absorbance was measured at 450 nm using a microtitre plate reader. The data generated in the assay is presented in Table 3. In order to determine the specificity of the competitive ELISAs, standard solutions of a range of structurally similar compounds were prepared in TBST. Using calibration curves generated from these compounds (0-80 ng/ml) percentage cross-reactivity was determined. The results of this study are presented in Table 4.

Chemicals

Chemicals were obtained from Cayman Chemical (2C-P, 2C-E, 2C-T-2 and 2,4,5-trimethoxyamphetamine), Sigma Aldrich (phenethylamine, methamphetamine and amphetamine), Toronto Research Chemicals (2C-D and 2C-C), LGC Limited (DOB, DOM, 2C-B and 2C-T-7); DON and 2C-CN were synthesised at Randox Laboratories. Chemicals used in synthetic procedures were sourced from Sigma Aldrich, Tokyo Chemical Industry Company Limited and Alfa Aesar.

Results

TABLE 1

Data generated from competitive microtitre plate assays for DOB, employing antisera generated to DOB-BSA

| | DOB | | |
|---|---|---|---|
| ng/ml | Ave OD (A450) | % CV | % B/Bo |
| 0 | 1.939 | 0.3 | 100.0 |
| 0.625 | 1.251 | 9.4 | 64.5 |
| 1.25 | 1.126 | 0.1 | 58.1 |
| 2.5 | 0.898 | 0.8 | 46.3 |
| 5 | 0.672 | 2.6 | 34.6 |
| 10 | 0.534 | 9.4 | 27.5 |
| 20 | 0.340 | 0.8 | 17.5 |
| 40 | 0.223 | 0.3 | 11.5 |
| IC50 | 2.013 | | |

$A_{450}$ = absorbance at 450 nm
B = absorbance at 450 nm at xng/ml standard concentration
$B_0$ = absorbance at 450 nm at 0 ng/ml standard concentration
Percentage B/B0 = (B/B0) × 100
$IC_{50}$ = standard concentration which produces 50% inhibition of maximal signal

TABLE 2

DO antibody cross-reactivity results (antibody 1) ($IC_{50}$ of the standard DOB is 2.01 ng/ml).

| Substance | % Cross-Reactivity |
|---|---|
| 1-(4-bromo-2,5-dimethoxyphenyl)propan-2-amine (DOB) | 100.0 |
| 1-(2,5-dimethoxy-4-methylphenyl)propan-2-amine (DOM) | 112.7 |
| 1-(2,5-dimethoxy-4-nitrophenyl)propan-2-amine (DON) | 43.1 |
| 2,4,5-trimethoxyamphetamine (TMA) | 9.8 |
| Dimethylamylamine | <1.0 |
| Methamphetamine | <1.0 |
| Amphetamine | <1.0 |
| (+)-Phenethylamine | <1.0 |
| 1-(4-bromo-2,5-dimethoxyphenyl)ethan-2-amine (2C-B) | <1.0 |
| 1-(2,5-dimethoxy-4-propylphenyl)ethan-2-amine (2C-P) | <1.0 |
| 1-(2,5-dimethoxy-4-ethylphenyl)ethan-2-amine (2C-E) | <1.0 |
| 1-(2,5-dimethoxy-4-ethylthiophenyl)ethan-2-amine (2C-T2) | <1.0 |
| 1-(4-chloro-2,5-dimethoxyphenyl)ethan-2-amine (2C-C) | <1.0 |
| 1-(2,5-dimethoxy-4-propylthiophenyl)ethan-2-amine (2C-T-7) | <1.0 |
| 1-(2,5-dimethoxy4-methylphenyl)ethan-2-amine (2C-D) | <1.0 |
| 1-(4-cyano-2,5-dimethoxyphenyl)ethan-2-amine (2C-CN) | <1.0 |

The compounds indicated below were also assessed for their cross-reactivity with the DO antibody 1 of the invention at the concentrations indicated in the Table below. No cross-reactivity (defined as <1% cross reactivity when compared with 100% for DOB) was detected at the indicated concentrations.

TABLE 2a

DO antibody additional cross-reactivity (antibody 1) results:

| Compound | ng/mL |
|---|---|
| 1,3-DMAA | 1000 |
| Mescaline | 100 |
| Amphetamine | 100 |
| Metamphetamine | 100 |
| MDMA | 100 |
| MDEA | 100 |
| BDB | 100 |
| MBDB | 100 |
| Phentermine | 100 |
| Mephedrone | 100 |
| Methcathinone | 100 |
| Tryptamine | 100 |
| Tyramine | 100 |
| R (+)-Cathinone HCl | 100 |
| S (−) Cathinone HCl | 100 |
| Pseudoephedrine | 100 |
| Phenylethylamine | 100 |
| Putrescine | 100 |

TABLE 2b

DO antibody additional cross-reactivity (antibody 2) results: $IC_{50}$ - 0.437 ng/mL

| Compound | % Cross reactivity |
|---|---|
| DOB | 100 |
| Bromo DragonFly (HCl)[1] | 96 |
| DOI HCl | 73 |
| DON | 57 |
| DOET | 50 |
| DOM | 49 |
| DOC (4-chloro-2,5dimethoxyamphetamine) | 47 |
| 2,4,5-trimethoxyampetamine | 5 |

Dragonfly is 1-(4-Bromofuro[2,3-f][1]benzofuran-8-yl)propan-2-amine

TABLE 3

Data generated from competitive microtitre plate assays for 2C-B, employing antisera generated to 2C-B-BSA

| | 2C-B | | |
|---|---|---|---|
| ng/ml | Ave OD (A450) | % CV | % B/Bo |
| 0 | 2.255 | 1.4 | 100.0 |
| 1.25 | 1.958 | 2.5 | 86.8 |
| 2.5 | 1.785 | 0.5 | 79.2 |
| 5 | 1.561 | 3.9 | 69.2 |
| 10 | 1.343 | 2.3 | 59.5 |
| 20 | 1.207 | 5.0 | 53.5 |
| 40 | 1.005 | 1.8 | 44.6 |
| 80 | 0.858 | 2.1 | 38.1 |
| IC50 | 24.618 | | |

$A_{450}$ = absorbance at 450 nm
B = absorbance at 450 nm at xng/ml standard concentration
$B_0$ = absorbance at 450 nm at 0 ng/ml standard concentration
Percentage B/B0 = (B/B0) × 100
$IC_{50}$ = standard concentration which produces 50% inhibition of maximal signal

TABLE 4

2C antibody cross-reactivity results ($IC_{50}$ of the standard 2CB is 24.6 ng/ml).

| Substance | % Cross-Reactivity |
|---|---|
| 2C-B | 100.0 |
| 2C-P | 276.8 |
| 2C-E | 178.8 |
| 2C-T-2 | 194.6 |
| 2C-C | 148.6 |
| 2C-T-7 | 171.0 |
| 2C-D | 308.3 |
| 2C-CN | 66.8 |
| DOB | <1.0 |
| (+)-Phenethylamine | <1.0 |
| Dimethylamylamine | <1.0 |

Tables 2 and 4 disclose the cross-reactivity profiles of antibodies to the DO and 2C sub-families.

The antibody described in Table 2 binds to DO sub-family members but not to 2C sub-family members or phenethylamine.

The antibody described in Table 4 binds to 2C sub-family members but not to DO sub-family members or phenethylamine.

The unique binding profiles of each antibody enables an immunoassay with unique sub-family cross-reactivity; such an immunoassay may take the form of one of the antibodies incorporated into an immunoassay kit for a singleplex assay or a spatially addressable substrate such as a biochip, or individualized fluorescent beads, incorporating both antibodies to enable a multiplex assay.

The invention claimed is:

1. A polyclonal antibody which specifically binds to 1-(4-bromo-2,5-dimethoxyphenyl)ethan-2-amine (2C-B), 1-(2,5-dimethoxy-4-propylphenyl)ethan-2-amine (2C-P), 1-(2,5-dimethoxy-4-ethylphenyl)ethan-2-amine (2C-E), 1-(2,5-dimethoxy-4-ethylthiophenyl)ethan-2-amine (2C-T2), 1-(4-chloro-2,5-dimethoxyphenyl)ethan-2-amine (2C-C), 1-(2,5-dimethoxy-4-propylthiophenyl)ethan-2-amine (2C-T-7), 1-(2,5-dimethoxy4-methylphenyl)ethan-2-amine (2C-D), and 1-(4-cyano-2,5-dimethoxyphenyl)ethan-2-amine (2C-CN), wherein the polyclonal antibody shows a cross-reactivity of less than 1.0% for each of 1-(4-bromo-2,5-dimethoxyphenyl)propan-2-amine (DOB), (+)-Phenethylamine, Dimethylamylamine, when compared to 100% cross-reactivity for 2C-B, wherein said cross reactivity is measured in the presence of a conjugate of structure:

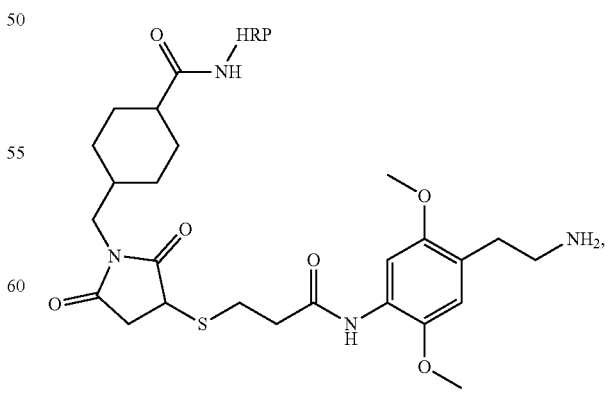

wherein the polyclonal antibody is derived from an immunogen of structure:

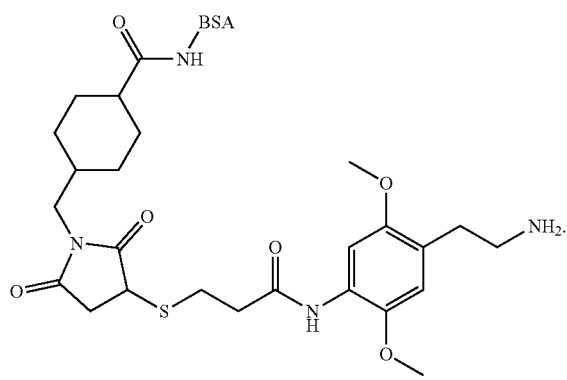

2. The polyclonal antibody of claim 1, wherein the polyclonal antibody shows a sensitivity ($IC_{50}$) of 24.618 ng/mL for 2C-B.

3. An immunoassay method of detecting phenethylamines of a 2C sub-family, the method comprising contacting a sample, with the polyclonal antibody of claim 1 and one or more detecting agents, and measuring a signal or signals produced by the one or more detecting agents; and deducing from a calibration curve the presence of, or amount of, phenethylamines of the 2C sub-family.

4. The immunoassay method of claim 3, wherein the one or more detecting agents are selected from the group consisting of an enzyme, a substance having fluorescent properties and a substance having a radioactive label.

5. The immunoassay method of claim 3, wherein the immunoassay method comprises a competitive assay format in which phenethylamines of the 2C sub-family compete with the one or more detecting agents in binding with the binding sites of the polyclonal antibody, wherein the more phenethylamines of the 2C sub-family present in the sample, the less detecting agent that binds to the polyclonal antibody and the lower the measured signal.

6. The immunoassay method of claim 5, wherein the one or more detecting agents comprise a detecting agent that has a structure that is similar to phenethylamines of the 2C sub-family in which an enzyme or a substance having fluorescent properties has been conjugated to the structure of the detecting agent.

7. The immunoassay method of claim 6, wherein the detecting agent has a structure of:

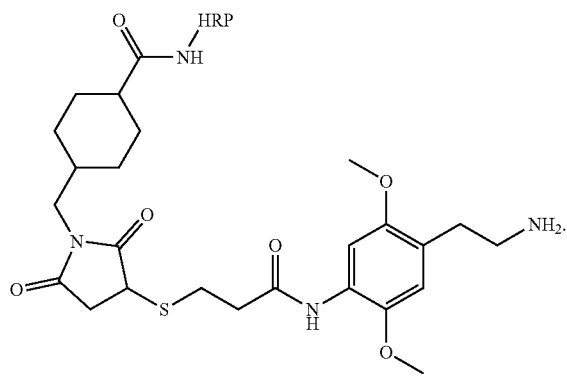

8. The immunoassay method of claim 3, wherein the sample is a blood, serum, plasma, urine or saliva sample.

9. The immunoassay method of claim 8, wherein the sample is a serum, plasma or urine sample.

10. The immunoassay method of claim 3, wherein the sample is from a human subject.

11. A substrate which comprises the polyclonal antibody of claim 1, wherein the polyclonal antibody is either absorbed to the substrate or attached to the substrate via covalent bonds.

12. The substrate of claim 11, wherein the substrate is a biochip.

13. The substrate of claim 11, wherein the substrate further comprises a second polyclonal antibody, wherein the second polyclonal antibody specifically binds to 1-(4-bromo-2,5-dimethoxyphenyl)propan-2-amine (DOB), 1-(2,5-dimethoxy-4-methylphenyl)propan-2-amine (DOM), and 1-(2,5-dimethoxy-4-nitrophenyl)propan-2-amine (DON), wherein the second polyclonal antibody shows a cross-reactivity of less than 1.0% for each of Dimethylamylamine, Methamphetamine, Amphetamine, (+)-Phenethylamine, 1-(4-bromo-2,5-dimethoxyphenyl)ethan-2-amine (2C-B), 1-(2,5-dimethoxy-4-propylphenyl)ethan-2-amine (2C-P), 1-(2,5-dimethoxy-4-ethylphenyl)ethan-2-amine (2C-E), 1-(2,5-dimethoxy-4-ethylthiophenyl)ethan-2-amine (2C-T2), 1-(4-chloro-2,5-dimethoxyphenyl)ethan-2-amine (2C-C), 1-(2,5-dimethoxy-4-propylthiophenyl)ethan-2-amine (2C-T-7), 1-(2,5-dimethoxy4-methylphenyl)ethan-2-amine (2C-D), 1-(4-cyano-2,5-dimethoxyphenyl)ethan-2-amine (2C-CN), when compared to 100% cross-reactivity for DOB, wherein said second polyclonal antibody cross reactivity is measured in the presence of a conjugate of structure

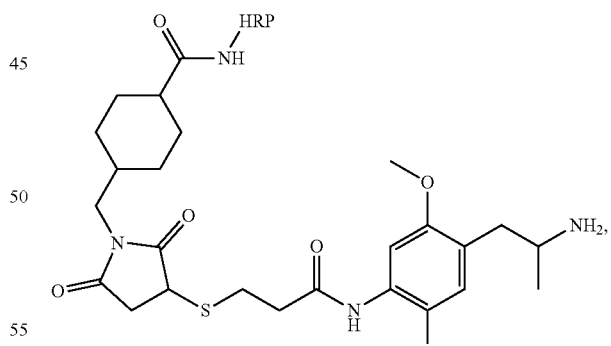

wherein the second polyclonal antibody is either absorbed to the substrate or attached to the substrate via covalent bonds, and wherein the second polyclonal antibody is derived from an immunogen of structure:

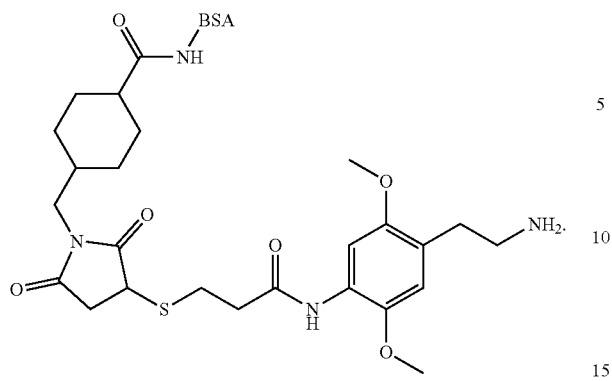
\* \* \* \* \*